United States Patent [19]

Birchmore et al.

[11] 4,250,179
[45] Feb. 10, 1981

[54] METAL COMPLEX IMIDAZOLE FUNGICIDES, AND METHODS OF CONTROLLING FUNGI WITH THEM

[75] Inventors: Richard J. Birchmore, Hucknall; Robert F. Brookes, Tollerton; Leonard G. Copping, Southwell; Wilfred H. Wells, Radcliff-on-Trent, all of England

[73] Assignee: The Boots Company Limited, Nottingham, England

[21] Appl. No.: 890,765

[22] Filed: Mar. 27, 1978

[30] Foreign Application Priority Data

Mar. 26, 1977 [GB] United Kingdom ............... 12828/77

[51] Int. Cl.$^3$ ........................ A01N 55/02; C07F 1/08; C07F 13/00
[52] U.S. Cl. .................................. 424/245; 548/101; 548/341; 424/273 R
[58] Field of Search ................ 260/299; 548/341, 101; 424/245, 273 R

[56] References Cited

U.S. PATENT DOCUMENTS

| 4,005,083 | 1/1977 | Büchel ................................ 424/245 |
| 4,080,462 | 3/1978 | Brookes et al. .................. 424/273 R |
| 4,118,461 | 10/1978 | Miller .................................. 424/273 |

FOREIGN PATENT DOCUMENTS 2429523 1/1975 Fed. Rep. of Germany .
2812662 9/1978 Fed. Rep. of Germany .

Primary Examiner—Donald G. Daus
Assistant Examiner—Diana G. Rivers
Attorney, Agent, or Firm—Lawrence Rosen

[57] ABSTRACT

New fungicidal compounds, and compositions of them and their uses and manufacture are described. The compounds are fungicidal complexes of a metal salt with certain, N,N-disubstituted carbamoyl imidazoles.

11 Claims, No Drawings

METAL COMPLEX IMIDAZOLE FUNGICIDES, AND METHODS OF CONTROLLING FUNGI WITH THEM

This invention relates to new compounds that are active as fungicides.

The compounds of the invention are fungicidal complexes of a metal salt with a compound of the formula

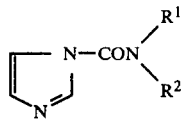

in which $R^1$ is an alkyl group and $R^2$ is a benzyl group or a phenoxyalkyl group, the benzyl and phenoxyalkyl groups being optionally substituted in the phenyl ring.

The compounds are the product of reacting a compound of formula I with a metal salt which is preferably one of the formula $MA_2$ in which M is a divalent metal cation and A is an anion. Examples of suitable metal ions, in the divalent state, include magnesium, calcium, copper, manganese, nickel, iron or cobalt, and of these copper and manganese are the most preferred.

The compounds may be represented by the formula

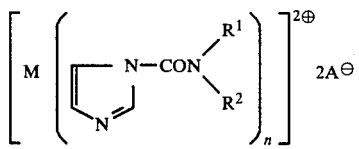

in which the symbols have the meanings given them above and n is 2 or 4, the preferred complexes being those in which n is 2.

These compounds have fungicidal activity against a wide range of fungi which attack agricultural crops. For example they can be used to control powdery mildew (*Erysiphe graminis*) and glume blotch (*Septoria nodorum*) on crops such as wheat, barley and oats and other fungal diseases of cereal crops such as leaf spot (*Pyrenophora avenae*) on oats, leaf stripe (*Pyrenophora graminae*) on barley, snow mould (*Fusarium nivale*) on rye and blast (*Pyricularia oryzae*) on rice. Many horticultural crops can also be treated with the compounds of the invention for example in the protection of fruit crops against *Botryis cinerea,* powder mildew (*Podosphaera leucotricha*) and scab (*Venturia inaequalis*) on apple trees, powdery mildew (*Sphaerotheca pannosa*) on roses, powdery mildew (*Sphaerotheca fuliginea*) on cucurbits and various fungal diseases on legumes such as beans, soybeans and peanuts. Treatment can be by means of direct application of the active compound to the crop, to the soil surrounding the crop or, in countering seed borne diseases, by seed dressing.

In addition to their uses in the treatment of agricultural crops the compound find many applications as general fungicides in, for example, the industrial sphere where materials such as paints, adhesives, starch, pastes, textiles, insulation, oils, pulp and paper products often need protection against attack by fungi. They are of particular value whenever their use or formulation involves mixing the compound with a powdered solid carrier.

Compounds of formula I preferably have the following structure

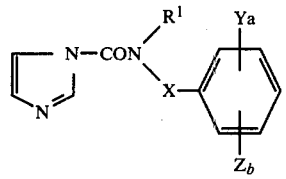

in which $R^1$ is alkyl containing 2 to 4 carbon atoms, X is the group $-CH_2-$ or $-(CH_2)_2O-$, Y is halo, a is 0 to 4, Z is an alkyl group containing 1 to 3 carbon atoms and b is 0 or 1. An especially preferred group is one in which X is $-(CH_2)_2O-$, Y is halo, a is 2, 3 or 4, Z is an alkyl group containing 1 to 3 carbon atoms and b is 0 or 1 and these latter compounds can be represented by the formula

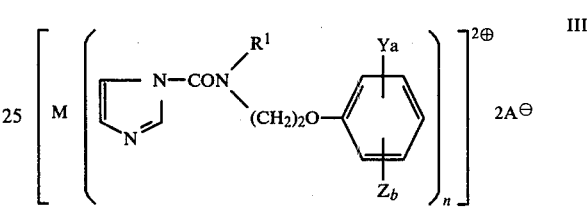

in which M is a divalent metal cation selected from magnesium, calcium, copper, manganese and nickel, n is 2 or 4, A is a monovalent anion, Y is halo, a is 2, 3 or 4, Z is an alkyl group containing 1 to 3 carbon atoms and b is 0 or 1. As mentioned above, the symbol n is preferably 2 and M is preferably copper or manganese.

In formulae II and III above $R^1$ can be ethyl, propyl, isopropyl, butyl, isobutyl or tert. butyl, Y can be, for example, chloro, bromo or iodo, bearing in mind that the Y groups, if there are more than one, need not be identical. The group Z can be, for example, methyl, ethyl or propyl and is especially methyl. When X is $-(CH_2)_2O-$ as in formula III there are preferably three substitutents on the ring, Y being chloro and Z methyl. The most preferred complexes are those derived from the compound 1-[N-propyl-N-2-(2,4,6-trichlorophenoxy)ethylcarbamoyl]imidazole, having the structure

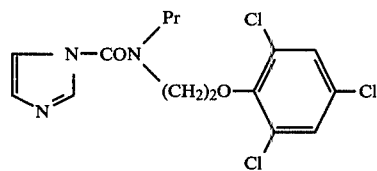

The anion can be any one of a wide range of organic and inorganic anions and examples include the chloride, bromide, fluoride, nitrate, formate, acetate, a sulphonate ion such as for example methanesulphonate, benzenesulphonate or p-toluenesulphonate ions. When the compound is to be used on crops the anion must be suitably non-phytotoxic. Preferred examples are the halides and nitrates, and especially the chloride ion. The complementary metal ion is chosen from the group comprising magnesium, calcium, copper, manganese, nickel, iron and cobalt, the most preferred being the copper (II) and manganese (II) ions.

A preferred example of the compounds according to the invention is the complex formed by the reaction of cupric or manganous chlorides with the compound of formula IV above, which can be shown as follows

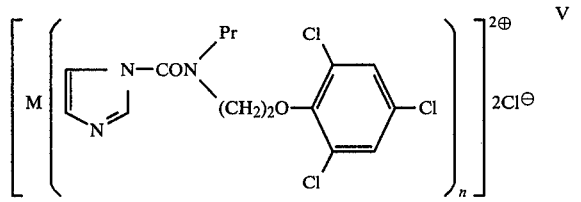

where M is copper or manganese and n is 2 or 4. These compounds, which can also be designated as the bis-[1-{N-propyl-N-2-(2,4,6-trichlorophenoxy)ethylcarbamoyl}imidazole] copper (II) or manganese (II) chloride complexes, are prepared in solid crystalline form and can be easily purified.

Compounds of formula I above are known and are included amongst those described, for example, in our British Pat. No. 1,469,772 where their method of preparation and properties are disclosed. The compounds of the invention are distinct chemical entitles with different physical properties from the free imidazole compounds of formula I. The latter are, in the main, liquid or semi-solid compounds, whereas the compounds of the invention are well-defined solids, usually having a melting point above 80° C. and often above 100° C.

A difficulty with the parent imidazole compounds of formula I is that they tend to be difficult to handle and especially to formulate with a solid powder carrier. Generally they must first be absorbed on to a carrier before a powder can be prepared. This tends to lower the fungicide activity as well as adding a further step to the method of manufacture. Because of the need to employ large quantities of solid carrier the compounds of formula I cannot conveniently be prepared in highly concentrated form.

The compounds of the invention however can be more readily handled and more readily formulated with a solid carrier, especially as a concentrate, than the parent compounds without any loss or any significant loss, in fungicidal activity. It is of particular value that they can be easily formulated as powder compositions since this is often the form most convenient for use as a dust, a seed dressing, or as a dispersible powder for addition to water before application to the crop.

We have also discovered that compounds of the invention, and in particular for example the compounds of formula V, have advantages when applied to broad-leaf crops. It has been observed that in some circumstances the parent imidazole compound of formula I tends to damage such crops and this is undesirable in however small a degree it occurs. The compounds of the invention surprisingly overcome this phytotoxic effect and are completely safe on susceptible crops. Crops where particular benefit is obtained are fruit trees, especially deciduous top fruit (eg applies, cherries and peaches), vines, legumes (eg peanuts and soya bean) and cucurbits (eg cucumbers, melons and courgettes). Preferred crops are fruit trees, peanuts and cucurbits.

The compounds of the invention can readily be prepared by reacting an imidazole of formula I with the appropriate metal salt, in an organic solvent containing medium, for example an alcoholic aqueous solution or dichloromethane. Most suitably the reactants are mixed together in stoichiometric or approximately stoichiometric proportions, that is in a molar ratio of 2:1 or 4:1 (imidazole compound to metal salt) depending on whether it is desired to prepare the complex with two or four ligands respectively. The reaction temperature is conveniently chosen within the range of from 10° to 40° C., for example from 20° to 30° C.

According to a further feature of the invention there is provided a fungicidal composition which comprises a compound of the invention together with a carrier. The active compound can be employed as a wide variety of formulations, for example, as an aqueous dispersion, a dispersible powder, a seed dressing, granules or a dust.

As a dispersion the composition comprises an active compound together with a dispersing agent dispersed in a liquid medium, preferably water. It can be in the form of a concentrated primary composition which requires dilution with a suitable quantity of water or other diluent before application. Such primary compositions are a convenient way of supplying the consumer and a preferred example is a dispersible powder. A dispersible powder comprises an active compound, a dispersing agent and a solid carrier. The latter can be for example kaolin, talc or diatomaceous earth and, in addition, the dispersible powder can contain a wetting agent.

Other formulations include seed dressings, granules or dusts, in all of which the active compound is associated with a solid carrier and which are intended for direct application. They can be made by methods well known in the art. Preferably all compositions comprising a solid carrier are made by mixing the active compound in particulate form with a particulate carrier.

The concentration of the active compound in the composition of the invention can vary widely. In the case of a primary composition it is preferably from 15 to 95 percent by weight, more especially from 50 to 80 percent by weight. A composition intended for direct application to a crop preferably comprises from 0.001 to 10 percent, more especially from 0.005 to 5 percent by weight, of the active compound, although when aerial spraying of a crop is contemplated compositions having a higher concentration, for example, up to 30 percent by weight may be chosen in preference.

Also included in the invention is a method for controlling a phytopathogenic fungus which comprises applying to seeds, plants or their habitat a compound of the invention. For convenience and effectiveness it is preferred to apply the active compound in the form of a composition as described above.

In the method of the invention the compound is applied to seeds, plants or their habitat. Thus the active compound can be applied directly to the plant by, for example, spraying or dusting either at the time when the fungus has begun to appear on the plant, or before the appearance of fungus as a protective measure. In both such cases the preferred mode of application is by foliar spraying. It is generally important to obtain good control of fungi in the early stages of plant growth as this is the time when the plant can be most severely damaged. For cereal crops such as wheat, barley and oats it is often desirable to spray the plant at or before growth stage 5 (Feeke's Scale) although additional treatments by spraying when the plant is more mature can augment resistance to the growth or spread of fungi. Sometimes, it is practicable to treat the roots of a plant before or during planting, for example, by dipping the roots in a suitable liquid or solid composition. When the active compound is applied directly to the plant a suitable rate of application is from 0.01 to 10 kilograms per hectare preferably from 0.05 to 5 kilograms per hectare.

Alternatively the compound can be applied directly to the soil at the same time as drilling so that the presence of active compound in the soil controls the growth of fungi which attack the seed. When the soil is treated directly the active compound can be applied in any manner which allows it to be intimately mixed with the soil by applying the active ingredient at the same time as drilling, inserting it in the same drill as the seeds. A suitable application rate is within the range of from 0.1 to 10 kilograms per hectare.

In a further method of the invention the active compound can be applied to the seed as a dressing in order to combat seed-borne diseases. This method is of particular use in the treatment of cereal grain against attack by, for example, leaf spot of oats and leaf stripe of barley. When the cereal grain is stored in a store-room or container the store-room or container can be treated with the active compound instead of, or in addition to, treatment of the cereal grain itself. A suitable rate of application for a seed dressing is from 0.05 to 5 grams per kilogram, such as for example from 0.1 to 1 grams per kilogram.

A more particular method of the invention is one for controlling fungal diseases on a cereal crop, such as for example wheat, barley, oats or rye which comprises applying to the crop a compound of the invention. For any particular compound it is necessary to choose the most effective method from amongst those described above at a suitable rate of application ensuring fungus control.

The invention is illustrated by the following Examples.

EXAMPLE 1

This Example illustrates the preparation of compounds according to the invention.

(1) To a solution of 35.13 g 1-[N-propyl-N-2-(2,4,6-trichlorophenoxy)ethylcarbamoyl]imidazole in 267 ml ethanol was added dropwise over a period of twenty-five minutes, a solution of 11.3 g cupric chloride ($CuCl_2.2H_2O$) in 30 ml of water. On completion of the addition the reaction mixture was stirred at room temperature for a further 2½ hours.

The solid product was isolated, washed with water and then with ether. After drying under vacuum it was dissolved in the minimum volume of dry dichloromethane at room temperature, charcoaled and filtered by gravity. Then at least an equal volume of dry ether was added to the filtered solution. On seeding and standing a solid deposited. It was collected and dried under vacuum at room temperature giving bis-[1-{N-propyl-N-2-(2,4,6-trichlorophenoxy)ethylcarbamoyl}imidazole] copper (II) chloride complex, as a green-blue crystalline solid, melting point 142°–144° C.

(2) The 1-[N-propyl-N-2-(2,4,6-trichlorophenoxy)ethylcarbamoyl]imidazole employed in the above reaction was prepared in the following manner.

A mixture of 197.5 g 2,4,6-trichlorophenol, 107.8 ml 1,2-dibromoethane and 500 ml water were stirred under reflux whilst sodium hydroxide solution (63 ml caustic soda liquor, specific gravity 1.5, and 61 ml water) was added slowly. The reaction mixture was heated under reflux for 16 hours and then the excess dibromoethane removed as an azeotrope, initially at atmospheric pressure and then under reduced pressure. To this mixture was then added 85 ml toluene and the temperature was maintained at about 50° C. The organic layer was separated and washed with dilute aqueous sodium hydroxide.

To this organic layer was added 85 ml toluene, 137 ml sodium hydroxide (specific gravity 1.5), 137 ml water and 134 ml propylamine. The reagents were stirred at 50° to 60° C. for eight hours and then left at room temperature for 60 hours. The aqueous layer was separated and the organic layer was distilled at atmospheric pressure and then under reduced pressure.

The distillate was slowly added to 39.7 g phosgene dissolved in 370 ml ice-cold toluene, keeping the temperature below 15° C. The mixture was then warmed to 70° C. and more phosgene passed in until a clear solution was formed. Toluene was removed under reduced pressure and the remaining solution cooled in ice. The solid formed was filtered off.

This toluene solution was diluted with a further quantity of 250 ml toluene and stirred at 80° C. for two hours with 47.3 g imidazole and 96.0 g anhydrous potassium carbonate. The mixture was allowed to cool and 386 ml water added. The organic layer was separated, washed with water and then dried over anhydrous magnesium sulphate. This was then concentrated under reduced pressure, stirred with dilute hydrochloric acid and the aqueous layer adjusted to pH 8 and ether extracted to give 1-[N-propyl-N-2-(2,4,6-trichlorophenoxy)ethylcarbamoyl]imidazole.

The following compounds were made by a similar method employing the appropriate imidazole compound and metal salt as reactants.

bis-[1-{N-2-(2,4-dichloro-6-methoxylphenoxy)ethyl-N-propylcarbamoyl}imidazole]manganese (II) chloride complex, melting point 132°–134° C.

bis-[1-{N-butyl-N-2-(2,4-dichloro-6-methylphenoxy)ethylcarbamoyl}imidazole]copper (II) chloride complex, melting point 136°–138° C.

bis-[1-{N-butyl-N-2-(4-chloro-2,6-dibromophenoxy)ethylcarbamoyl}imidazole]copper (II) chloride complex, melting point 168°–169° C.

bis-[1-{N-propyl-N-2-(2,4,6-trichlorophenoxy)ethylcarbamoyl}imidazole]copper (II) bromide complex, melting point 151°–153° C.

bis-[1-{N-2-(2-bromo-4-chlorophenoxy)ethyl-N-butylcarbamoyl}imidazole]copper (II) chloride complex, melting point 130°–132° C.

bis-[1-{N-propyl-N-2-(2,4,6-trichlorophenoxy)ethylcarbamoyl}imidazole]copper (II) nitrate complex, melting point 124°–126° C.

bis-[1-{N-2-(2,4-dichloro-6-methylphenoxy)ethyl-N-propylcarbamoyl}imidazole]copper (II) chloride complex melting point 130°–132° C.

bis-[1-{N-2-(2,4-dichloro-6-methylphenoxy)ethyl-N-propylcarbamoyl}imidazole]nickel chloride complex, melting point 158°–160° C.

bis-[1-{N-propyl-N-2-(2,4,6-trichlorophenoxy)ethylcarbamoyl}imidazole]iron (II) chloride complex, melting point 136°–138° C.

bis-1-(N-2-phenoxyethyl-N-propylcarbamoyl)imidazole copper (II) chloride complex, melting point 125°–127° C.

bis-[1-(N-2,4-dichlorobenzyl-N-isopropylcarbamoyl)imidazole]copper (II) chloride complex, melting point 78°–80° C.

EXAMPLE 2

The method described in Example 1 was used to prepare a complex having four imidazole ligands by reacting 7.5 g 1-[N-propyl-N-2-(2,4,6-trichlorophenoxy) ethylcarbamoyl]imidazole in 50 ml ethanol with 0.85 g cupric chloride in 7 ml water. When washed with water and ether, crude tetrakis-[1-{N-propyl-N-2-(2,4,6-trichlrorophenoxy)ethylcarbamoyl}imidazole] copper (II) chloride complex was collected. This material was further purified using dry methylene dichloride, charcoal and dry ether as described in Example 1 to give the product, melting point 133°–134° C.

EXAMPLE 3

This Example describes the preparation of bis-[1-{N-propyl-N-2-(2,4,6-trichlorophenoxy)ethylcarbamoyl}-imidazole] manganese (II) chloride complex.

To 79 g manganous choride ($MnCl_2.4H_2O$) in 600 ml ethanol was added 300 g 1-[N-propyl-N-2-(2,4,6-trichlorophenoxy)ethylcarbamoyl]imidazole dissolved in 840 ml ethanol. The reaction mixture was stirred at room temperature for eighteen hours and then allowed to stand at room temperature for two days, filtered by suction and then washed with water. This product was then dried under vacuum at 50° C. to give bis-[1-{N-propyl-N-2-(2,4,6-trichlorophenoxy)ethylcarbamoyl}-imidazole]manganese (II) chloride complex, melting point 137°–139° C.

EXAMPLE 4

This Examples describes the preparation of tetrakis-[1-{N-2-phenoxyethyl-N-propylcarbamoyl}imidazole]-manganese (II) chloride complex.

A stirred solution of 10.92 g 1-[N-2-phenoxyethyl-N-propylcarbamoyl]imidazole in 30 ml ethanol was added dropwise at room temperature, to a solution of 1.98 g manganous chloride ($MnCl_2.4H_2O$) in 20 ml ethanol. On completion of the addition the reaction mixture was stirred at room temperature for a further three hours resulting in a homogeneous solution. The solvent was then removed by rotary evaporation at 30° C. and 2 mm pressure for a period of two hours, a syrupy residue being obtained. This was then triturated with ether, a cream coloured solid being obtained. It was washed with ether and dried under vacuum at room temperature, tetrakis-[1-{N-2-phenoxyethyl-N-propylcarbamoyl}imidazole]manganese (II) chloride complex, melting point 86° to 88° C.

The following compound was prepared by a similar route: tetrakis-[1-{N-2,4-dichlorobenzyl-N-isopropylcarbamoyl}imidazole]manganese (II) chloride complex, melting point 167° to 169° C.

EXAMPLE 5

A wettable powder formulation was prepared by mixing together the following substances

| bis-[1-{N-propyl-N-2-(2,4,6-trichlorophenoxy)ethylcarbamoyl} imidazole]manganese (II) chloride complex | |
|---|---|
| | 25.0% |
| Monolan PB* | 3.0% |
| Dyapol PT** | 5.0% |
| kaolin | to 100.0% by weight |

*a complex ethylene oxide-propylene oxide copolymer
**a sulphated condensate of urea, cresol and formaldehyde Similar formulations to the above are prepared by substituting the above active compound with the same quantity of any of the compounds of the invention described in Examples 1 to 4.

EXAMPLE 6

A wettable powder formulation was prepared by mixing together the following substances

| bis-[1-{N-propyl-N-2-(2,4,6-trichlorophenoxy)ethylcarbamoyl} imidazole]manganese (II) chloride complex | |
|---|---|
| | 70.0% |
| Dyapol PT | 7.5% |
| Aerosol OTB* | 1.0% |
| kaolin | to 100.0% by weight |

*sodium dioctylsulphosuccinate

EXAMPLE 7

A wettable powder formulation was prepared by mixing together the following substances

| bis-[1-{N-propyl-N-2-(2,4,6-trichlorophenoxy)ethylcarbamoyl} imidazole]copper (II) chloride complex | |
|---|---|
| | 71.0% |
| Reax 88B* | 10.0% |
| Aerosol OTB | 1.0% |
| kaolin | to 100.0% by weight |

*a mixture of sodium lignosulphate and wetting agent.

EXAMPLE 8

A seed dressing was prepared with the following ingredients

| bis-[1-{N-propyl-N-2-(2,4,6-trichlorophenoxy) ethylcarbamoyl}imidazole]manganese (II) chloride complex | |
|---|---|
| | 10.0% |
| Lake Red Toner (dye) | 1.0% |
| light liquid paraffin | 2.0% |
| talc | to 100.0% by weight |

Similar seed dressings are prepared by substituting the above compound with the same quantity of any of the compounds of the invention described in Examples 1 to 4.

EXAMPLE 9

The following ingredients were employed in the preparation of a granular formulation

| bis-1-[N-2-phenoxyethyl-N-propylcarbamoyl]imidazole copper (II) chloride complex | |
|---|---|
| | 5.0% |
| Ethylan BV* | 1.0% |
| fuller's earth | 94.0% |

*an alkylphenol ethoxylate

EXAMPLE 10

This Example illustrates the fungicidal activity of the compounds of the invention when used to control mildew on barley.

In one set of experiments barley seedlings were infected with cereal powdery mildew, *Erysiphe graminis,* and subsequently sprayed with a suspension of test compound at a concentration of 1000 parts per million.

In a further set of experiments barley seedlings were first sprayed with the suspension of test compound at 1000 parts per million and the treated seedlings then inoculated with powdery mildew.

A visual assessment was made of the infection, if any, that resulted, and a comparison made with untreated barley seedlings. All of the compounds of the invention described in Examples 1 to 4 gave greater than 50 percent control of mildew in both of these tests.

EXAMPLE 11

This Example illustrates the activity of compounds of the invention in controlling *Boytryis cinerea*.

A quantity of agar containing 2 percent malt extract was sterilised in an autoclave. The material (20 ml) was dispensed into a boiling tube containing sufficient of the active compound to give a concentration of 5 parts per million, after stirring to ensure uniform distribution. The contents of the boiling tube were then poured into a Petri dish and allowed to solidify. A spore suspension in sterile distilled water was prepared and the agar inoculated with it. After incubating the agar for a period of one week it was examined to assess the growth of the fungus and compared with control experiments in which the active compound had been omitted from the agar medium. Measurements of the diameter of the fungal growth were compared with controls and all of the following compounds showed a reduction in diameter of at least 50 percent:

bis-[1-{N-propyl-N-2-82,4,6-trichlorophenoxy)ethylcarbamoyl}imidazole]copper (II) chloride complex bis-[1-{N-propyl-N-2-(2,4,6-trichlorophenoxy)ethylcarbamoyl}imidazole]manganese (II) chloride complex bis-[1-{N-propyl-N-2-(2,4,6-trichlorophenoxy)ethylcarbamoyl}imidazole]copper (II) bromide complex bis-[1-{N-butyl-N-2-(4-chloro-2,6-dibromophenoxy)ethylcarbamoyl}imidazole]copper (II) chloride complex tetrakis-[1-{N-propyl-N-2-(2,4,6-trichlorophenoxy)ethylcarbamoyl}imidazole]copper (II) chloride complex bis-[1-{N-propyl-N-2-(2,4,6-trichlorophenoxy)ethylcarbamoyl}imidazle]copper (II) nitrate complex bis-[1-{N-2-(2,4-dichloro-6-methylphenoxy)ethyl-N-propylcarbamoyl}imidazle]copper (II) chloride complex bis-[1-{N-2-(2,4-dichloro-6-methylphenoxy)ethyl-N-propylcarbamoyl}imidazole]nickel chloride complex bis-1-{N-2-(2,4-dichloro-6-methylphenoxy)ethyl-N-propylcarbamoyl}imidazole]manganese (II) chloride complex bis-[1-{N-butyl-N-2-(2,4-dichloro-6-methylphenoxy)ethylcarbamoyl}imidazole]copper (II) chloride complex bis-[1-{N-propyl-N-2-(2,4,6-trichlorophenoxy)ethylcarbamoyl}imidazle]iron (II) chloride complex.

We claim:

1. A solid fungicidal compound of the formula

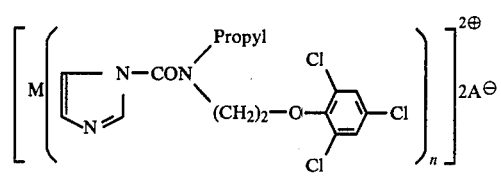

in which M is copper or manganese, n is 2 or 4, and A is chloride.

2. A fungicidal compound according to claim 1 wherein M is copper.

3. A fungicidal compound according to claim 1 wherein M is manganese.

4. A solid fungicidal composition comprising a fungicidally effective amount of a complex compound having the formula:

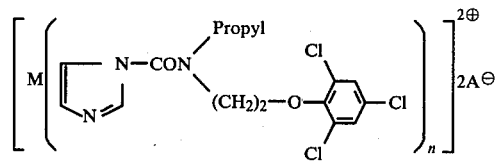

in which M is copper or manganese, n is 2 or 4, and A is chloride; and a fungicidally acceptable carrier.

5. A fungicidal composition according to claim 4 wherein M is copper.

6. A fungicidal composition according to claim 4 wherein M is manganese.

7. A fungicidal composition according to claim 4 wherein the carrier is particulate solids.

8. A fungicidal composition according to claim 1 wherein the composition is in the form of dispersible powders, dusts, and seed dressings.

9. A method for controlling a phytopathogenic fungus which comprises applying to seeds, plants and their habitat the compound according to claim 1.

10. A method according to claim 9 for controlling a fungal disease on a cereal crop which comprises applying the compound to the crop.

11. A method according to claim 9 comprising applying the compound to a broad leaf crop selected from fruit trees, vines, legumes and cucurbits.

* * * * *